United States Patent [19]

Helminen et al.

[11] Patent Number: 6,147,235

[45] Date of Patent: Nov. 14, 2000

[54] PROCESS FOR HYDROGENATING UNSATURATED PLANT-BASED COMPOUNDS AND REGENERATION OF A USED CATALYST

[75] Inventors: Jarkko Helminen; Ulf Hotanen, both of Lappeenranta; Erkki Paatero, Kauniainen; Matti Hautala; Ari Kärki, both of Lappeenranta, all of Finland

[73] Assignee: UPM-Kymmene OYJ, Lappeenranta, Finland

[21] Appl. No.: 09/142,743

[22] PCT Filed: Mar. 14, 1997

[86] PCT No.: PCT/FI97/00170

§ 371 Date: Sep. 15, 1998

§ 102(e) Date: Sep. 15, 1998

[87] PCT Pub. No.: WO97/34917

PCT Pub. Date: Sep. 25, 1997

[30] Foreign Application Priority Data

Mar. 15, 1996 [FI] Finland ..................... 961242

[51] Int. Cl.[7] ........................................ C07J 9/00
[52] U.S. Cl. ............................................. 552/544
[58] Field of Search ............................. 552/544; 562/512, 562/513, 606

[56] References Cited

U.S. PATENT DOCUMENTS

| 3,865,853 | 2/1975 | Hinze | 260/409 |
|---|---|---|---|
| 4,427,591 | 1/1984 | Ayer et al. | 260/397.45 |
| 5,326,825 | 7/1994 | Nasman et al. | 525/301 |
| 5,412,127 | 5/1995 | Mentink et al. | 554/212 |

FOREIGN PATENT DOCUMENTS

| 0629441 | 12/1994 | European Pat. Off. . |
|---|---|---|
| 38 00 563 | 3/1989 | Germany . |
| 38 00 564 | 3/1989 | Germany . |
| 39 25 359 | 2/1991 | Germany . |
| 39 25 360 | 2/1991 | Germany . |
| 41 10 705 | 10/1992 | Germany . |
| 41 10 706 | 12/1992 | Germany . |
| 42 25 978 | 4/1994 | Germany . |
| 44 05 029 | 8/1995 | Germany . |
| 1260037 | 1/1972 | United Kingdom . |
| 1301300 | 12/1972 | United Kingdom . |

OTHER PUBLICATIONS

E.N. Frankel et al., "Hydrogenation of methyl Sorbate and Soybean Esters with Polymer–bound Metal Catalysts", pp. 349–354, American Oil Chemists Society Campaign, IL, Journal vol. 57, No. 10, 1980.

B. Gordon III et al., "Rhodium(I) Catalyst Supported on Polymer Crystal Surfaces: Further Hydrogenation Studies", pp. 2139–2142, Journal of Polymer Science: part A: Polymer Chemistry, vol. 25, 1987.

*Primary Examiner*—Barbara Badio
*Attorney, Agent, or Firm*—Young & Thompson

[57] ABSTRACT

The invention relates to a process for catalytic hydrogenation of non-hormonal unsaturated plant steroids and unsaturated plant-based fatty acids and triglycerides thereof using a metal catalyst bound to a polymer support containing grafted groups. The invention also relates to regeneration of a used catalyst.

12 Claims, 1 Drawing Sheet

PROCESS FOR HYDROGENATING UNSATURATED PLANT-BASED COMPOUNDS AND REGENERATION OF A USED CATALYST

CROSS REFERENCE TO RELATED APPLICATION

This is the 35 USC 371 national stage of international application PCT/FI97/00170 filed on Mar. 14, 1997 which designated the United States of America.

FIELD OF THE INVENTION

The invention relates to a process for hydrogenating unsaturated plant-based compounds with a polymer-bound catalyst containing grafted groups. The invention further relates to regeneration of a catalyst. The term 'unsaturated plant-based compounds' refers herein to non-hormonal unsaturated plant steroids and to unsaturated fatty acids and their triglycerides.

BACKGROUND OF THE INVENTION

Steroids are macromolecular, non-volatile and thermosensitive organic compounds with a complicated structure. They are used for many special purposes: as pharmaceuticals, additives in foodstuffs, cosmetic products, etc. They are often produced on a small scale, and the same multipurpose reactor is used in steroid syntheses for various reactions, such as hydrogenation, oxidation, reduction and esterification.

Steroids are a group of compounds with a similar structure. They are commonly present in plants and animals and include, for example, sterols, vitamin D, bile acids and sex hormones. The structure of steroids is based on the following 1,2-cyclopentenofenanthrene ring system:

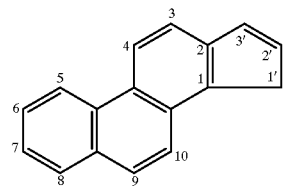

Sterols are steroids whose structure contains an OH group. Sterols are crystalline $C_{26}$–$C_{30}$ compounds, and they contain an aliphatic side chain at $C_{17}$. Sterols occur in the nature either as free sterols or as esters of higher fatty acids. Sterols can be isolated from the non-saponifiable moiety of fats and oils. The best known animal sterol (zoosterol) is cholesterol. The best known plant sterols (phytosterols) are stigmasterol, sitosterol and ergosterol (yeast sterol). The structure of cholesterol is illustrated by the following formula:

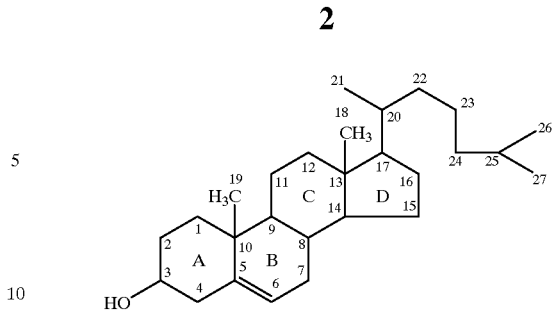

The stereochemistry of the substituents at carbon atoms 3 and 10 is important for the hydrogenation of the $\Delta^5$-double bond. If the hydroxyl group at $C_3$ and the methyl group at $C_{10}$ are both above the ring, they are at a cis-position in relation to each other. In steroids, a group of substituents above the ring is indicated with β, whereas a group of substituents below the ring is indicated with α. In all plant sterols, the hydroxyl and methyl group are at a β-position.

The structure of sitosterol differs from that of cholesterol only in that in sitosterol there is an ethyl group attached to $C_{24}$. The double bond of sitosterol and cholesterol is called a $\Delta^5$-bond. Cholesterol is also known by the name of 5-cholesten-3β-ol, and sitosterol by the name of 24α-ethyl-5-cholesten-3β-ol.

Catalytic hydrogenation is a common intermediate step in steroid syntheses, for example. It is used for reducing various functional groups or for hydrogenating double bonds. Whether a hydrogenation is successful depends on whether the product is stereochemically correct. If the product is stereo-specifically incorrect, it is not suitable for further syntheses or for the actual application. The hydrogenation process of the invention is used for preparing steroids in which the H-atom at $C_5$ is at an α-position.

According to the prior art, steroids have been hydrogenated by means of nickel black, Raney nickel, and nickel catalysts attached to inorganic supports. The activity of nickel metal has, however, not been sufficient for hydrogenating steroid double bonds. Steroids have also been hydrogenated with noble metal catalysts, particularly Pd- and Pt-catalysts. Hydrogenations have been carried out by the use of metal blacks, or noble metal catalysts bound to inorganic supports or to activated carbon. The best conversions of the starting material have been achieved with noble metal catalysts bound to activated carbon, particularly with the Pd/C-catalyst. It is generally known that the problems with the use of such a catalyst have been the separation of particulate catalyst powder from the reaction mixture after hydrogenation, the inflammability of the catalyst, and the fact that the catalyst is not recyclable.

Until the 1960's, the catalyst most commonly used for hydrogenating the $\Delta^5$-double bond of steroids was platinum. In syntheses, platinum has been used in the form of Adams Pt-oxide. The Adams Pt-oxide is a hydrogenation catalyst prepared in situ by reducing platinous dioxide with hydrogen to platinum metal.

At the end of the 1960's, it was found that the most efficient catalyst in hydrogenation of steroid double bonds was palladium. Hydrogenation of cholesterol with a Pd/C-catalyst in ethanol at room temperature and under a normal atmosphere gave a cholestanol yield of 85 to 95%. This is a better yield than has been obtained with Pt-oxide in ethyl acetate and cyclohexane, and much better than has been obtained with Pt-oxide in acetic acid.

Cholesterol has been hydrogenated with Pt, Rh, Ir, Ru, Os, and Pd metals in a competing reaction with α-pinene. The reaction rate of cholesterol in relation to α-pinene was 1.2 with Pd, whereas with Os the reaction could not be detected, and with the other metals the relative reaction rate was of the order of 0.12 to 0.16. The strong reaction of steroids with a Pd-catalyst is a result of their high adsorption to the surface of palladium. Particularly the α-surface of steroids has a high ability to adsorb to palladium.

Pt-oxide can be used if the hydrogenolysis of other functional groups is to be avoided in the hydrogenation of steroid double bonds. Raney nickel or platinum is recommended when the migration of the double bond presents a problem. The pure 5α-form has been obtained in the hydrogenation of a $\Delta^5$-double bond by the use of Raney nickel, Pt-oxide or copper chrome oxide.

Hydrogenation of unsaturated oils and fats involves hydrogenation of numerous double bonds in an aliphatic chain. The hydrogenation reaction of fats and oils is complicated because of simultaneously occurring isomerization of unsaturated bonds. Vegetable oils are triglycerides of fatty acids and contain one, two, three or even more unsaturated bonds in each fatty acid.

The most important acids for hydrogenation are, for example, linolenic, linolic and oleic acid, all of which contain 18 carbon atoms. Linolenic acid is a fatty acid containing three double bonds: one at the 9th, 12th and 15th bond. Linolic acid contains two double bonds: one at the 9th and 12th bond. Oleic acid, in turn, contains one double bond at the 9th bond. The end product of the hydrogenation of these fatty acids is stearic acid, which is a saturated molecule containing 18 carbon atoms.

Hydrogenation is a way of converting liquid oils into semi-solid plastic fats suited for the production of fat products and margarines. Hydrogenation also has other desirable properties: it improves the stability and colour of the fat, for example.

Metals that are catalytically active in the hydrogenation of double bonds of fatty acid molecules include Fe, Co, Ni, Pd, Pt, Cu, Ag and Au. Nickel-based catalysts have been used most in processes for hydrogenating oils. The problem with the use of a nickel catalyst has been insufficient selectivity. In addition, nickel catalysts have not been suitable for selective hydrogenation from linolenic acid to linolic acid.

It is known that the aim in catalyst studies has long been to develop a catalyst that possesses the advantages of both a homogeneous and a heterogeneous catalyst. A homogeneous catalyst, i.e. a liquid catalyst in liquid phase hydrogenation, gives almost always better selectivity and activity than a heterogeneous catalyst, i.e. a solid catalyst in hydrogenation, which in turn has better separability. Although it is easier to separate a heterogeneous catalyst from a reaction mixture after hydrogenation than a homogeneous one, it is often still too complicated, since in order to obtain sufficient activity, it is necessary to use particulate catalyst powders. The aim in developing polymer-bound catalysts has been to combine the advantages of homogeneous and heterogeneous catalysis.

Polymer-bound catalysts have many advantages. They have higher activity than conventional heterogeneous catalysts, since the active sites of the catalyst are isolated from each other, and ligand-bridged complexes are not formed. Polymer-bound catalysts also have better selectivity on account of the larger steric environment. In addition, the catalyst losses are smaller than with conventional catalysts.

Polymer-bound catalysts are clearly more expensive than conventional catalysts, wherefore the support must be selected such that the catalyst can be recycled. The support must also be mechanically strong in order for the catalyst to endure even vigorous mixing. The physical structure of the support must be suitable to allow as many functional groups as possible to come into contact with the reaction mixture. In addition, the microenvironment of the support must be of the right kind and suitable for the reaction: it should possess, for example, the correct polarity, hydrophilicity and microviscosity.

In recent years, crosslinked polystyrene resins have been commonly used as supports for transition metal catalysts. However, their use is problematic, wherefore resin-bound catalysts cannot be used in industrial applications. The reaction rate is to a great extent dependent on the solvent which swells the polymer and allows the reactants access to the active sites of the catalyst. In addition, differences in polarity and changes in the size of the reactants may prevent diffusion in the resin.

Because of the problems with polystyrene resins, new polymer support materials have been searched for in recent years. Polyolefins, particularly polyethylene and polypropylene, used as support materials, have proved to be promising. The Wilkinson homogeneous catalyst, for example, is attached to a polyethylene crystal and to a microporous polyethylene hollow fibre by chemical methods. The process for preparing these catalysts is complicated, and therefore not suitable for production of catalysts on a large scale.

A catalyst is deactivated in use, when its activity or selectivity decreases from the original level. The deactivation may result from poisoning, fouling or sintering of the catalyst, or from the loss of the active component. Sulphur is one of the most common substances which poison metal catalysts.

Regeneration is a treatment for restoring the original activity of a catalyst.

Regeneration of a deactivated polymer-supported metal catalyst has not been reported in the prior art.

SUMMARY OF THE INVENTION

It is an object of the present invention to provide a process for hydrogenating non-hormonal unsaturated plant steroids and unsaturated plant-based fatty acids and triglycerides thereof catalytically with hydrogen. The invention further relates to regeneration of a catalyst used in the hydrogenation process.

The process of the invention can be applied to hydrogenation of all unsaturated non-hormonal plant-based steroids. These steroids cover, for instance, all wood-based unsaturated steroids found in the neutral fraction of pulping and steroids isolated from plants, such as β-sitosterol and campesterol and all their cleavage products, such as sitostene. The length of the side chains of steroid molecules may vary.

The hydrogenation process of the invention can also be applied to hydrogenation of unsaturated plant-based fatty acids. These cover, for example, all fatty acids contained by tall oil and its distillation products, and fatty acids contained by vegetable oils, e.g. linolic, linolenic and oleic acids.

The hydrogenation process of the invention is characterized in that the catalyst is a metal catalyst bound to a polymer support containing grafted groups.

The polymer support of the catalyst is a polymer containing grafted groups, preferably a polymer grafted with monomeric and/or polymeric groups. A preferred polymer support can also be defined as a graft polymer or a graft copolymer.

A particularly preferred polymer support is a polyolefin polymer onto which monomeric and/or polymeric groups are grafted. The monomeric groups used for the grafting may be, for example, acrylic acid groups, and the polymeric groups may be, for example, polyacrylic acid groups. They may also be methacrylic acid, polymethacrylic acid, styrene or polystyrene groups.

The polyolefin used as a preferred polymer support can be illustrated with the formula —$CH_2$—CHR wherein R is H, or $(CH_2)_n CH_3$ wherein n is 0 to 20. Examples of such polyolefins are polyethylene and polypropylene. The support polymer may also be a halogenated polyolefin —$CX_2$—$CX_2$— wherein X is H or halogen or a mixture of them. Examples of such polyolefins are polyvinylidenefluoride and polytetrafluoroethylene. The grafting reagents can be illustrated with the formula —$CH_2$—$CR_1$—(COOH) wherein $R_1$ is H or $CH_3$ or with the formula

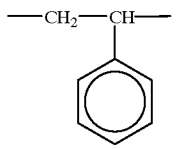

The metal attached to the catalyst is preferably a transition metal, particularly Ni, Pd, Pt, Rh or Ru, or a mixture thereof. The amount of metal used per polymer support is usually 5 to 10%.

The weight ratio between the grafting reagent and the polymer support may vary within the range of 0.5 to 20, but usually it is 1 to 6. The molar ratio between the metal and the grafting reagent is 0.001 to 0.5, preferably 0.01 to 0.1.

The catalyst bound to the polymer support in the catalytic hydrogenation of the invention may be in the form of a film, fibre, sphere, cylinder, saddle, ring, or in any other form of a pellet, or a hollow fibre or membrane. Most preferably the catalyst is in the form of separate fibres, or a felt or wire, for example.

The particle size of the catalyst may vary. When a fibre-like catalyst is used, the thickness of the catalyst fibres may be, for example, 10 to 300 μm and their length may be 0.1 to 10 cm.

The polymeric catalyst used in the hydrogenation process of the invention may be prepared, for instance, by the pre-irradiation grafting process disclosed in U.S. Pat. No. 5,326,825. It is a two-step process in which only the polymer is irradiated at first under a nitrogen atmosphere, and subsequently the irradiated polymer is grafted in a monomer solution. The preparation of the catalyst comprises the following steps: (a) exposing a polymer, e.g. a polyethylene polymer, to irradiation by a linear accelerator under a nitrogen atmosphere, (b) immersing the irradiated polymer in a monomer solution (e.g. an aqueous solution of acrylic acid), (c) separating the resulting graft polymer, (d) loading a metal onto the polymer, and (e) reducing the catalyst.

In the hydrogenation process of the invention, it is possible to use, for example, a commercially available catalyst (manufactured by SMOPTECH Oy, Turku, Finland) in which palladium metal (e.g. 5% or 10%) is bound to a polypropylene or polyethylene polymer fibre support grafted with acrylic acid. This catalyst is prepared by the process disclosed in U.S. Pat. No. 5,326,825.

The catalyst used in the process of the invention can be treated with water before the hydrogenation in order to swell it. Swelling increases the area of the catalyst and enhances its efficiency, as the reaction rate increases.

The hydrogenation reaction of the invention can be carried out in a solvent or without a solvent. A neutral organic solvent, such as alcohol (e.g. methanol, ethanol, n-propanol, isopropanol or t-butanol) or cyclohexane, is preferably used in stereoselective hydrogenation of steroids to the α-form.

Fatty acids can be hydrogenated either with a solvent or without it. The solvent may be an organic solvent, such as the monoethyl ether of ethylene glycol.

The hydrogenation pressure may be 0.5 to 10 bar, preferably about 1 to 3 bar, expressed as overpressure. A pressure of 1 bar is sufficient for hydrogenating double bonds that are easy to hydrogenate, whereas double bonds that are rather difficult to hydrogenate can be hydrogenated under a pressure of a few bars.

The hydrogenation temperature may vary from room temperature to about 200° C., depending on the pressure. Double bonds that are easy to hydrogenate can be hydrogenated at room temperature, but double bonds that are more difficult to hydrogenate require a higher temperature and/or pressure. The reaction rate increases as the temperature rises. A preferred hydrogenation temperature for steroids is about 60 to 80° C., and for fatty acids about 80 to 160° C.

The reaction time may be 0.5 to 24 hours, most usually it is of the order of a few hours.

The amount of the starting material to be hydrogenated of the total amount of the reaction mixture may vary with steroids e.g. from 1 to 30% by weight, depending on the solvent, and with fatty acids from 1 to 100% by weight.

The hydrogenation may be carried out in various types of reactors, e.g. in a fixed bed reactor or a stirred tank reactor. The reactor may be a batch reactor or a continuous reactor.

After the hydrogenation reaction, the catalyst is separated by filtration, and the hydrogenation product is separated usually by crystallization.

In the process of the invention, the catalyst can be easily separated from the hydrogenation product, there are no fire risks, and the formation of side products in the hydrogenation reaction is minimized on account of better selectivity. The process can be carried out under a relatively low pressure.

The hydrogenation process of the invention can also be combined with regeneration of a used catalyst. The invention further relates to this additional process step for regenerating the catalyst. The use of an expensive catalyst requires recyclability of the catalyst, which is made possible by the regeneration process of the invention.

The regeneration process of the invention comprises the characterizing step of oxidating the used catalyst at an elevated temperature. The oxidation can be performed in a solvent, e.g. water, or without a solvent. The oxidation is carried out under an oxygenous atmosphere. 'Elevated temperature' refers to a temperature of about 50 to 200° C., preferably 110 to 115° C. The regeneration time is usually of the order of a few hours, and the pressure is normal atmosphere. The regeneration can also be carried out under an elevated pressure, i.e. an overpressure of 0.1 to 10 bar.

'Oxygenous atmosphere' refers preferably to air. It is also possible to use air concentrated with oxygen.

Before and after the oxidation, the catalyst is washed preferably with water. It is also possible to use an organic solvent, or a mixture of water and an organic solvent.

In practice, the regeneration of a catalyst usually comprises the following steps: (a) washing in boiling water, (b) filtering, (c) oxidating under an oxygenous atmosphere, (d) washing with boiling water, and (d) filtering.

When a palladium catalyst, for example, is used, a small amount of sulphur is removed from the catalyst during the first washing step of the regeneration. In the oxidation step, the palladium sulphide in the catalyst is oxidated to water-soluble palladium sulphate. The water-soluble sulphate can be easily removed by washing in the second washing step without removing the palladium metal.

DETAILED DESCRIPTION OF THE INVENTION

Figure 1:
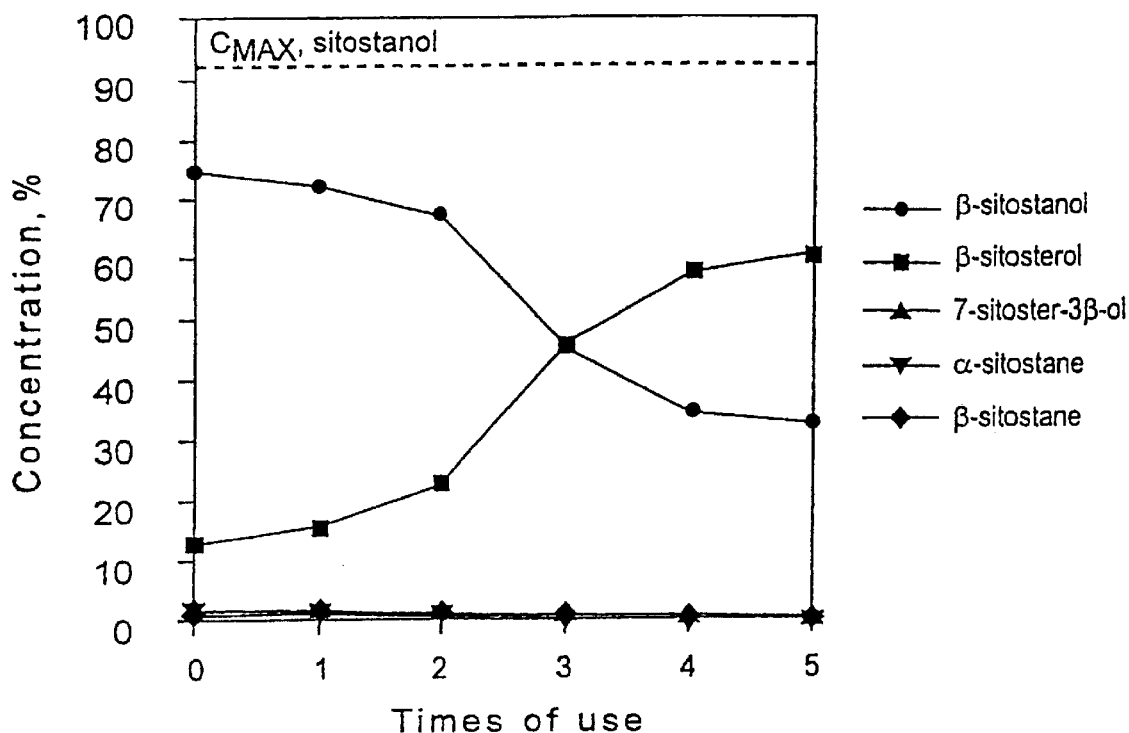
FIG. 1 shows composition of a product in a test series in which the catalyst was washed in n-propanol after hydrogenation.

The following examples are intended to illustrate the hydrogenation process of the invention, and the regeneration of the catalyst used in the hydrogenation.

EXAMPLE 1

A palladium-loaded acrylic-acid-grafted polypropylene polymer fibre support catalyst which contained 10% by weight of palladium metal (catalyst prepared by the process disclosed in U.S. Pat. No. 5,326,825 and manufactured by SMOPTECH Oy, Turku, Finland) was used for hydrogenating, on a pilot scale with a batch reactor having a volume of 336 l, 15 kg of a steroid mixture containing 78.3% β-sitosterol, 13.6% β-sitostanol, 5.1% campesterol and 0.6% campestanol in 135 kg n-propanol. The amount of catalyst was 300 g, the reaction temperature was about 60° C., the total pressure was an overpressure of about 1 bar, and the mixing about 180 min$^{-1}$. The main product of the hydrogenation of β-sitosterol (SSTRL) was β-sitostanol (SSTNL). The hydrogenation reaction is illustrated by the following scheme:

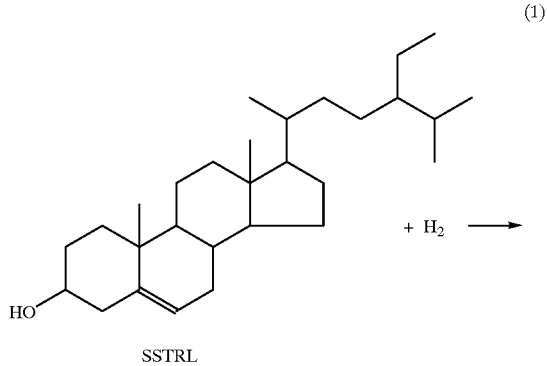

(1)

Campesterol (CSTRL) is hydrogenated to campestanol (CSTNL):

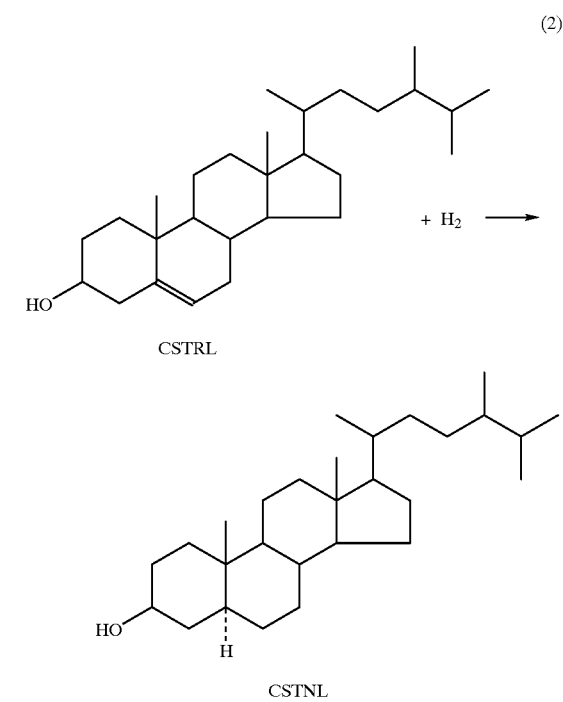

(2)

After a hydrogenation of 8.5 h, the mixture had the following steroid composition: 3.7% β-sitosterol, 85.1% β-sitostanol, 1.4% campesterol, and 5.4% campestanol.

EXAMPLE 2

A catalyst was used in which 10% by weight of palladium metal (catalyst prepared by the process disclosed in U.S. Pat. No. 5,326,825 and manufactured by SMOPTECH Oy, Turku, Finland) had been bound to a polyethylene polymer fibre support grafted with acrylic acid. The catalyst was used for hydrogenating, on a pilot scale with a batch reactor having a volume of 336 l, 15 kg of a steroid mixture containing 77.9% β-sitosterol, 13.3% β-sitostanol, 6.3% campesterol and 0.7% campestanol in 135 kg n-propanol. The amount of catalyst was 300 g, the reaction temperature was 60 to 80° C., the total pressure was an overpressure of 0.9 to 3.5 bar, and the mixing about 180 min$^{-1}$. After a hydrogenation of 6 h, the mixture had the following steroid composition: 5.4% β-sitosterol, 82.4% β-sitostanol, 1.6% campesterol and 6.3% campestanol.

EXAMPLE 3

A catalyst prepared in the same way as in Example 2 was used. The catalyst was used for hydrogenating, on a laboratory scale with a batch reactor having a volume of 1.0 l, 50 g of a steroid mixture containing 77.4% β-sitosterol, 12.5% β-sitostanol, 6.7% campesterol and 0.7% campestanol in 450 g isopropanol. The amount of Pd-metal in the catalyst was 0.5% by weight of the amount of the steroid starting material, the amount of the steroid starting material was 10% by total weight of the reaction mixture, the reaction temperature was 80° C., the total pressure was an overpressure of about 1 bar, and the mixing about 600 min$^{-1}$. After a hydrogenation of 2 h, the mixture had the following steroid composition: 0.9% β-sitosterol, 81.1% β-sitostanol, 0.8% campesterol and 6.8% campestanol.

EXAMPLE 4

A catalyst in which 5% by weight of palladium metal (catalyst prepared by the process disclosed in U.S. Pat. No. 5,326,825 and manufactured by SMOPTECH Oy, Turku, Finland) had been bound to a polyethylene polymer fibre support grafted with acrylic acid was used for hydrogenating, on a laboratory scale with a batch reactor having a volume of 1.0 l, 50 g of a steroid mixture containing 78.6% β-sitosterol, 11.9% β-sitostanol, 6.4% campesterol and 0.6% campestanol in 450 g isopropanol. The amount of Pd-metal in the catalyst was 0.1% of the amount of the steroid starting material, the amount of the steroid starting material was 10% by total weight of the reaction mixture, the reaction temperature was 80° C., the total pressure was an overpressure of about 3 bar, and the mixing about 600 min$^{-1}$. After a hydrogenation of 2 h, the mixture had the following steroid composition: 22.9% β-sitosterol, 66.7% β-sitostanol, 2.2% campesterol and 5.4% campestanol.

EXAMPLE 5

A catalyst prepared in the same way as in Example 2 was used. The catalyst was used for hydrogenating, on a laboratory scale with a batch reactor having a volume of 1.0 l, 20 g of a steroid mixture containing 78.0% β-sitosterol, 13.4% β-sitostanol, 6.1% campesterol and 0.7% campestanol in 180 g cyclohexane. The amount of Pd-metal in the catalyst was 2% by weight of the amount of the steroid starting material, the amount of the steroid starting material was 10% by total weight of the reaction mixture, the reaction temperature was 60° C., the total pressure was an overpressure of about 1 bar, and the mixing about 300 min$^{-1}$. After a hydrogenation of 1 h, the mixture had the following steroid composition: 12.5% β-sitosterol, 74.0% β-sitostanol, 1.9% campesterol and 5.6% campestanol.

EXAMPLE 6

A catalyst prepared in the same way as in Example 2 was used. The catalyst was used for hydrogenating, on a laboratory scale with a batch reactor having a volume of 1.0 l, 50 g of a steroid mixture containing 79.8% β-sitosterol, 11.3% β-sitostanol, 6.5% campesterol and 0.7% campestanol in 450 g n-propanol. The same catalyst was used for six hydrogenations with the same starting material under the same reaction conditions. After the hydrogenation, the catalyst was separated from the product by filtering and washed in boiling n-propanol, the weight ratio between the catalyst and solvent being 1:60. The reaction conditions in all hydrogenations were as follows: the amount of Pd-metal in the catalyst was 0.2% of the amount of the steroid starting material, the amount of the steroid starting material was 10% by total weight of the reaction mixture, the reaction temperature was 70° C., the total pressure was an overpressure of about 3 bar, and the mixing about 600 min$^{-1}$. The composition of the product in successive hydrogenations thus performed is shown in FIG. 1. FIG. 1 thus shows composition of the product in a test series in which the catalyst was washed in n-propanol after hydrogenation.

Deactivation of the catalyst in successive hydrogenations can be seen from FIG. 1. No significant mass losses of the catalyst took place during the six hydrogenations.

EXAMPLE 7

Figure 2:
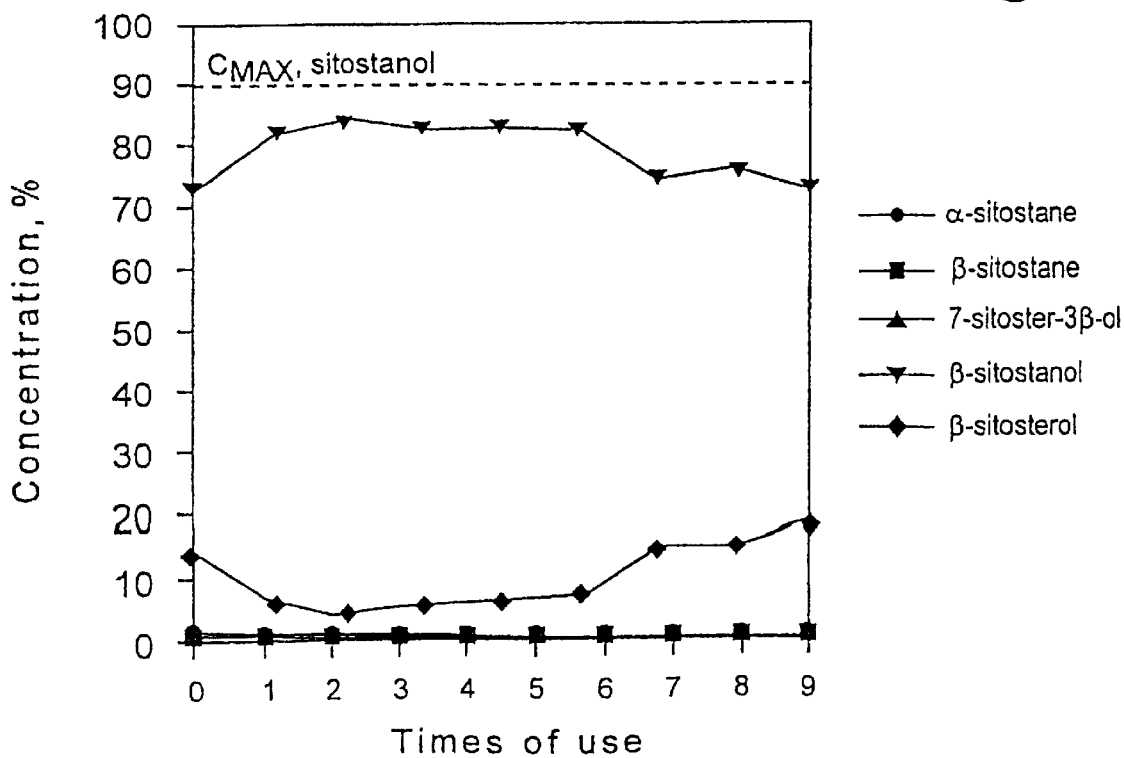
FIG. 2 shows composition of the product in a test series in which the catalyst was regenerated between hydrogenations by washing it in boiling water, oxidizing it at 110° C., and washing it again in boiling water.

A catalyst prepared in the same way as in Example 2 was used. The catalyst was used for hydrogenating, on a laboratory scale with a batch reactor having a volume of 1.0 l, 50 g of the same steroid mixture as in Example 6 in 450 g n-propanol. The same catalyst was used for eight hydrogenations with the same starting material under the same reaction conditions. The hydrogenation conditions were the same as in Example 6. After the hydrogenations, the catalyst was washed in boiling water for 10 min, the weight ratio between the catalyst and water being 1:60. After the washing, the catalyst separated from the water by filtering was oxidated at 110° C. under an oxygenous atmosphere for 3 h, after which the catalyst was washed in water in the same way as in the first washing. After the second washing, the catalyst separated from water by filtering was loaded for the next hydrogenation while still wet with water. The composition of the product in successive hydrogenations thus performed is shown in FIG. 2. FIG. 2 thus shows composition of the product in a test series in which the catalyst was regenerated between hydrogenations by washing it in boiling water, oxidating it at 110° C., and finally washing it again in boiling water.

Deactivation of the catalyst could be prevented by the process described in the example. The slight reduction in activity which occurred during the last hydrogenations was a result of catalyst losses: after the eighth hydrogenation, only 73% of the original amount of the catalyst was left.

EXAMPLE 8

The effect of the washing and oxidation steps of the regeneration on the sulphur content of the catalyst was studied in industrial scale test runs by a catalyst which was deactivated. The amount of catalyst taken for each laboratory test was 2.5 g, and the catalyst was subjected to the regeneration shown in Table I. After the regeneration, the sulphur contents of the catalysts were analyzed by a bomb method.

TABLE I

Regeneration processes for studying the reduction in the sulphur content of the catalyst.

| Test | Regeneration method |
|---|---|
| R100 | No regeneration. |
| R101 | 1) Washing for 10 min in ion-exchanged water.<br>2) Oxidating at 110° C. for 3 h.<br>3) Washing for 20 min in ion-exchanged water. |

Table II shows the results of the analyses.

TABLE II

Sulphur content of a catalyst poisoned in a test on industrial scale after regeneration.

| Sample | S-content, ppm |
|--------|----------------|
| R100   | 300            |
| R101   | 55             |

On the basis of the results shown in Table II, it is obvious that the sulphur content of the catalyst is reduced in regeneration.

EXAMPLE 9

A catalyst prepared in the same way as in Example 2 was used. The catalyst was used for hydrogenating, on a pilot scale with a batch reactor having a volume of 336 l, 15 kg of a steroid mixture containing 78.2% β-sitosterol, 12.2% β-sitostanol, 6.6% campesterol and 0.6% campestanol in 135 kg n-propanol. The amount of catalyst was 300 g, the reaction temperature was 70 to 80° C., the total pressure was an overpressure of about 3.2 bar, and the mixing about 180 $min^{-1}$. When the same catalyst was used for the seventh time after a hydrogenation for 5 h, the mixture had the following steroid composition: 25.1% β-sitosterol, 64.3% β-sitostanol, 2.9% campesterol and 5.3% campestanol. After this, the same catalyst was used for four hydrogenations with the same starting material under the same reaction conditions. Before each hydrogenation, the catalyst was regenerated by washing it for 30 min in 20 kg of boiling water, oxidating it for 4 h at 115° C., and washing it for a second time for 30 min in 20 kg of boiling water. Even in the eleventh hydrogenation, the same catalyst gave the following steroid composition after a hydrogenation for 4.5 h: 1.5% β-sitosterol, 84.4% β-sitostanol, 1% campesterol and 6.9% campestanol.

EXAMPLE 10

A catalyst prepared in the same way as in Example 2 was used. The catalyst was used for hydrogenating, on a laboratory scale with a batch reactor having a volume of 0.3 l, a solution containing 100 g of fatty acids, and 50 g of monoethyl ether of ethylene glycol. The fatty acid solution used in the hydrogenation contained 63.3% by weight of linolic acid, 20.1% by weight of oleic acid, and 5.5% by weight of stearic acid. The amount of catalyst was 0.5 g, the reaction temperature was 100° C., the total pressure was an overpressure of about 5.0 bar, and the rotation speed of the mixer about 600 $min^{-1}$. After a hydrogenation of 2 h, the fatty acid composition was as follows: 20.7% by weight of linolic acid, 59.8% by weight of oleic acid, and 9.0% by weight of stearic acid.

EXAMPLE 11

A catalyst prepared in the same way as in Example 2 was used. The catalyst was used for hydrogenating, on a laboratory scale with a batch reactor having a volume of 0.3 l, a solution containing 100 g of fatty acids and 50 g of monoethyl ether of ethylene glycol. The fatty acid solution used in the hydrogenation contained 10.2% by weight of linolic acid, 69.3% by weight of oleic acid, and 1.9% by weight of stearic acid. The amount of catalyst was 1.0 g, the reaction temperature was 110° C., the total pressure was about 4.0 bar overpressure, and the rotation speed of the mixer about 600 $min^{-1}$. After a hydrogenation of 2 h, the fatty acid composition was as follows: 1.2% by weight of linolic acid, 52.7% by weight of oleic acid, and 31.3% by weight of stearic acid.

EXAMPLE 12

A catalyst prepared in the same way as in Example 2 was used. The catalyst was used for hydrogenating, on a laboratory scale with a batch reactor having a volume of 0.3 $dm^3$, a solution containing 150 g of fatty and resin acids. The fatty and resin acid solution used in the hydrogenation contained 8.9% by weight of linolenic acid, 42.9% by weight of linolic acid, 32.8% by weight of oleic acid, and 1.5% by weight of stearic acid. The amount of catalyst was 2.5 g, the reaction temperature was 130° C., the total pressure was about 6.0 bar overpressure, and the rotation speed of the mixer about 600 $min^{-1}$. After a hydrogenation of 2 h, the fatty acid composition was as follows: 1.5% by weight of linolenic acid, 21.8% by weight of linolic acid, 72.8% by weight of oleic acid, and 1.5% by weight of stearic acid.

EXAMPLE 13

A catalyst prepared in the same way as in Example 2 was used. The catalyst was used for hydrogenating, on a laboratory scale with a batch reactor having a volume of 0.3 l, a solution containing 100 g of fatty acids and 50 g of monoethyl ether of ethylene glycol. The fatty acid solution used in the hydrogenation contained 64.8% by weight of linolic acid, 20.2% by weight of oleic acid, and 4.3% by weight of stearic acid. The amount of catalyst was 2.0 g, the reaction temperature was 130° C., the total pressure was about 6.0 bar overpressure, and the rotation speed of the mixer about 600 $min^{-1}$. With a catalyst partly deactivated after a hydrogenation of 2 h, the fatty acid composition was as follows: 24.4% by weight of linolic acid, 55.9% by weight of oleic acid, and 10.6% by weight of stearic acid. After this, the catalyst was regenerated by washing it for 15 min in 120 ml of boiling water, oxidating it for 3 h at 110° C., and washing it for a second time for 20 min in 120 ml of boiling water. After a hydrogenation of 2 h with the regenerated catalyst (1.78 g), the fatty acid composition was as follows: 14.0% by weight of linolic acid, 62.5% by weight of oleic acid, and 13.7% by weight of stearic acid.

EXAMPLE 14

A catalyst prepared in the same way as in Example 2 was used. The catalyst was used for hydrogenating, on a laboratory scale with a batch reactor having a volume of 1.0 l, 50 g of a steroid mixture containing 79.8% by weight of β-sitosterol, 11.3% by weight of β-sitostanol, 6.5% by weight of campesterol and 0.7% by weight of campestanol in 450 g n-propanol. Two hydrogenations were carried out, in which the amount of Pd-metal in the catalyst was 0.2% of the amount of the steroid starting material, the amount of the steroid starting material was 10% by total weight of the reaction mixture, the reaction temperature was 70° C., the total pressure about 3 bar overpressure, and the mixing 600 $min^{-1}$. Hydrogenation was performed with a catalyst supplied by the manufacturer of the catalyst under the conditions described above, whereby after 2 h, the steroid composition was as follows: 36.5% by weight of β-sitosterol, 54.4% by weight of β-sitostanol, 3.1% by weight of campesterol and 4.3% by weight of campestanol. A catalyst that was of the same lot as the one used in the previous test was used for hydrogenation under the same conditions as in the previous test. Prior to the hydrogenation, the catalyst was swollen by boiling it in water for 30 min, the weight ratio between the catalyst and the water being 1:60. After the swelling, the catalyst was separated from the water by filtering and loaded to hydrogenation while still wet. After a hydrogenation of 2 h, a catalyst treated in this way gave the following steroid composition: 14.3% β-sitosterol, 73.9% β-sitostanol, 1.6% campesterol and 6% campestanol.

The foregoing general discussion and experimental examples are intended to be illustrative of the present invention, and they are not to be considered limiting. Other variations within the spirit and scope of this invention are possible and will present themselves to those skilled in the art.

What is claimed is:

1. A process for hydrogenating non-hormonal unsaturated plant steroids catalytically with hydrogen, wherein the catalyst is a transition metal catalyst selected from the group consisting of Ni, Pd, Pt, Rh, Ru and mixtures thereof, and is bound to a polymer support selected from the group consisting of polyolefin and halogenated polyolefin, and containing grafted groups selected from the group consisting of acrylic acid, polyacrylic acid, methacrylic acid, polymethacrylic acid, styrene and polystyrene groups; and wherein the steroids are hydrogenated in a solvent, and the hydrogenation is carried out at an overpressure of 0.5 to 10 bar, and a temperature varying from room temperature to about 200° C.

2. The process according to claim 1, wherein the polyolefin is grafted with acrylic acid and/or polyacrylic acid groups.

3. The process according to claim 1, wherein the transition metal is palladium.

4. The process according to claim 1, wherein the catalyst is in the form of separate fibers, felt or wire.

5. The process according to claim 1, wherein the catalyst is swollen with water before use.

6. The process according to claim 1, wherein the hydrogenation is carried out at an overpressure of 1 to 3 bar.

7. The process according to claim 1, wherein steroids are hydrogenated at a temperature of about 60 to 80° C.

8. The process according to claim 1, wherein the solvent is a neutral organic solvent.

9. The process according to claim 8, wherein the solvent is isopropanol, n-propanol or cyclohexane.

10. The process according to claim 1 further comprising:

regeneration of the used catalyst by
oxidizing the catalyst at an elevated temperature; and
washing the catalyst with water before and after oxidation.

11. The process according to claim 10, wherein the oxidation is carried out under an oxygenous atmosphere at a temperature of about 50 to 200° C.

12. The process according to claim 11, wherein the oxidation is carried out in air at a temperature of about 110 to 115° C.

* * * * *